United States Patent
Yamamoto

(10) Patent No.: US 9,366,657 B2
(45) Date of Patent: Jun. 14, 2016

(54) METHOD FOR EXAMINING REACTION LAYER FOR FUEL CELL

(75) Inventor: Taizo Yamamoto, Sapporo (JP)

(73) Assignee: KABUSHIKI KAISHA EQUOS RESEARCH, Tokyo (JP)

( * ) Notice: Subject to any disclaimer, the term of this patent is extended or adjusted under 35 U.S.C. 154(b) by 127 days.

(21) Appl. No.: 14/236,143

(22) PCT Filed: Sep. 28, 2011

(86) PCT No.: PCT/JP2011/072287
§ 371 (c)(1),
(2), (4) Date: Mar. 27, 2014

(87) PCT Pub. No.: WO2013/046380
PCT Pub. Date: Apr. 4, 2013

(65) Prior Publication Data
US 2014/0370605 A1    Dec. 18, 2014

(51) Int. Cl.
*G01N 31/10* (2006.01)
*G01N 23/04* (2006.01)
*H01M 4/92* (2006.01)
(Continued)

(52) U.S. Cl.
CPC ............... *G01N 31/10* (2013.01); *G01N 23/04* (2013.01); *H01M 4/8605* (2013.01); *H01M 4/8668* (2013.01); *H01M 4/92* (2013.01); *H01M 8/1004* (2013.01); *H01M 2008/1095* (2013.01); *Y02E 60/521* (2013.01)

(58) Field of Classification Search
CPC ..... G01N 31/10; G01N 23/04; H01M 4/8605; H01M 4/8668; H01M 8/1004; H01M 4/92

USPC .................................. 436/2, 5, 37, 100, 119
See application file for complete search history.

(56) References Cited

U.S. PATENT DOCUMENTS 5,284,571 A * 2/1994 Verbrugge ................ C25B 9/10
                                                        205/118
8,263,286 B2    9/2012   Nakai et al.
(Continued)

FOREIGN PATENT DOCUMENTS

| JP | A 2006-140061 | 6/2006 |
| JP | A 2006-140062 | 6/2006 |

(Continued)

OTHER PUBLICATIONS

Park, M. J. et al, ECS Transactions 2008, 16, 1357-1363.*
(Continued)

*Primary Examiner* — Arlen Soderquist
(74) *Attorney, Agent, or Firm* — Oliff PLC

(57) ABSTRACT

The purpose of the present invention is to grasp the state in which hydrophilic groups of an electrolyte are distributed in a reaction layer for fuel cells. Nitric acid groups are bonded to hydrophilic groups (sulfonic acid groups) contained in a reaction layer for fuel cells, and metal ions capable of forming a nitrosyl complex with the nitric acid groups, e.g., ruthenium ions, are introduced into the reaction layer to dye the nitric acid groups bonded to the hydrophilic groups contained in the reaction layer. When the hydrophilic groups have agglomerated, the nitric acid groups bonded thereto also agglomerate. When said nitric acid groups are dyed with ruthenium, the ruthenium also agglomerates to make it possible to examine said nitric acid groups with an electron microscope.

3 Claims, 5 Drawing Sheets

$NO_3^-$ : Nitric acid ions

(51) Int. Cl.
  *H01M 4/86*     (2006.01)
  *H01M 8/10*     (2016.01)

(56) References Cited

U.S. PATENT DOCUMENTS

| | | | |
|---|---|---|---|
| 8,304,134 B2 | 11/2012 | Miyake et al. | |
| 2006/0180796 A1* | 8/2006 | Adachi | C09K 5/20 252/500 |
| 2008/0075999 A1* | 3/2008 | Izuhara | C08J 5/2218 429/450 |
| 2009/0124020 A1* | 5/2009 | Balogh | H01M 8/1004 436/164 |

FOREIGN PATENT DOCUMENTS

| | | |
|---|---|---|
| JP | A 2008-234844 | 10/2008 |
| JP | A 2008-243778 | 10/2008 |
| JP | A 2009-104905 | 5/2009 |
| JP | A 2010-7016 | 1/2010 |
| WO | WO 2008/102851 A1 | 8/2008 |
| WO | WO 2009/098982 A1 | 8/2009 |

OTHER PUBLICATIONS

Jan. 17, 2012 Search Report issued in International Patent Application No. PCT/JP2011/072287 (with translation).
Jan. 17, 2012 Written Opinion issued in International Patent Application No. PCT/JP2011/072287 (with translation).
Eikerling et al; "Electrochemical impedance of the cathode catalyst layer in polymer electrolyte fuel cells;" Journal of Electroanalytical Chemistry; 1999; vol. 475; pp. 107-123.
Makharia et al; "Measurement of Catalyst Layer Electrolyte Resistance in PEFCs Using Electrochemical Impedance Spectroscopy;" Journal of the Electrochemical Society; 2005; vol. 152; No. 5; pp. SA970-SA977.
Itagaki et al; "Electrochemical impedance method: Electrochemical impedance analysis using distributed constant type equivalent circuit;" 8; pp. 133-146 (with partial translation).

* cited by examiner

IT IS CONSIDERED THAT WHEN POLYMER ELECTROLYTE IS THICKLY ADHERED TO CATALYST, SULFONIC ACID GROUP WHICH IS NOT ORIENTED ON CATALYST SIDE MAY FORM "CLUSTER" AS ILLUSTRATED ABOVE.

NO₃⁻ : Nitric acid ions

NO₃⁻ : Nitric acid ions

METHOD FOR EXAMINING REACTION LAYER FOR FUEL CELL

TECHNICAL FIELD

The present invention relates to a method of observing a reaction layer of a fuel cell.

BACKGROUND ART

A membrane electrode assembly used in a fuel cell is configured that a solid polymer electrolyte membrane is held between a hydrogen electrode and an air electrode, and the hydrogen electrode and the air electrode are each configured that reaction layers and diffusion layers are stacked in sequence from the solid polymer electrolyte membrane side.

A reaction layer comprises a mixture of a catalyst and an electrolyte and is required to have conductivity of electrons and protons and air permeability. Since the proton moves in the form of $H_3O^+$ along with water, the reaction layer is required to be maintained in a wet state. Of course, when an excess water content is present in the reaction layer, the air permeability is inhibited (so-called flooding phenomenon), and therefore, the water content of the reaction layer is required to be always maintained at a suitable amount.

In order to satisfy the above requirement, the present applicant has proposed a catalyst paste having a thin water film between a catalyst and an electrolyte in Patent Documents 1 and 2. In order to obtain such a catalyst paste, a pre-paste containing a catalyst previously mixed with water is provided and then mixed with an electrolyte solution, and a suitable stirring method is employed. In such a catalyst paste thus formed, a hydrophilic group of the electrolyte is drawn to a water film covering a catalyst to face the water film, and a hydrophilic region is formed between the electrolyte and the catalyst. The hydrophilic region becomes a water film. Hereinafter, a structure having a hydrophilic region between a catalyst and an electrolyte in a mixture of the catalyst and the electrolyte is also referred to as a "PFF structure".

When the hydrophilic regions between the catalyst and the electrolyte are contiguous (namely, when the hydrophilic regions are not arranged in a spot-like pattern), uneven distribution of water in a reaction layer is prevented. Even when a fuel cell is operated in a low humidification environment, water is collectively present in the hydrophilic region, and therefore, overdrying can be prevented. In the operation in a high humidification environment, since excess water is discharged outside (toward a diffusion layer) through the hydrophilic region, flooding can be prevented.

See Patent Document 3 and Non-Patent Documents 1 to 3 as literature disclosing techniques related to the present invention.

PRIOR ART DOCUMENTS

Patent Documents

Patent Document 1: Japanese Patent Laid-Open Publication No. 2006-140061
Patent Document 2: Japanese Patent Laid-Open Publication No. 2006-140062
Patent Document 3: Japanese Patent Laid-Open Publication No. 2009-104905

Non-Patent Documents

Non-Patent Document 1: Journal of Electrochemical Society 2005, vol. 152, No. 5, PP. A970-A977 MAKHARIA Rohit; MATHIAS Mark F.; BAKER Daniel R. "Measurement of catalyst layer electrolyte resistance in PEFCs using electrochemical impedance spectroscopy"
Non-Patent Document 2: Journal of Electroanalytical Chemistry 475, 107-123 (1999) M. Eikerling and A. A. kornyshev "electrochemical impedance of Cathode Catalyst Layer of Polymer Electrolyte Fuel Cells"
Non-Patent Document 3: "Electrochemical impedance method" (Masayuki ITAGAKI, Maruzen) 8 Electrochemical impedance analysis using distributed constant type equivalent circuit (pp. 133 to 146)

SUMMARY OF THE INVENTION

Problems to be Solved by the Invention

Not only in the PFF structure, a path for water is required to be formed in order to secure the conductivity of a proton. In a material constituting a reaction layer, an essentially hydrophilic material is a hydrophilic group of an electrolyte (for example, a sulfone group), and the hydrophilic group is required to aggregate in the formation of the path for water in the reaction layer, and the aggregates are required to be continued.

In the above-described PFF structure, aggregates of the hydrophilic group are collected on a surface of a catalyst to form the path for water on the surface of the catalyst.

For example, when the hydrophilic group is dispersed, water adsorbed to the hydrophilic group is separated from each other, and the path for water is not formed. Thus, a proton supplied from the outside cannot be delivered. Furthermore, it is not preferable from the standpoint of draining excess generated water.

As described above, it is important to grasp a distribution state of the hydrophilic group of the electrolyte for understanding the properties of the reaction layer of the fuel cell. However, the prior art has not provided any method of grasping that.

Means for Solving the Problems

As a result of studies on a distribution state of a hydrophilic group of an electrolyte in a reaction layer, the present inventor has noticed that a functional group is made to have an affinity for the hydrophilic group of the electrolyte and is dyed with metal ions, whereby the distribution state of the hydrophilic group can be observed with a microscope to complete the present invention.

Namely, a first aspect of the present invention is specified as follows.

A method of observing a fuel cell reaction layer comprising:
a step of making a functional group to have an affinity for a hydrophilic group of an electrolyte constituting a reaction layer of the fuel cell; and
a step of introducing a metal ion capable of forming a complex with the functional group to the reaction layer and dyeing the functional group with the metal ions.

According to this observation method, the hydrophilic group of the electrolyte is dyed with the metal ions, although it is dyed indirectly through the functional group, and therefore, the distribution state of the hydrophilic group can be visually observed with a microscope.

An electrolyte used in a reaction layer of a fuel cell is formed of a polymer compound, and a fluorine-based polymer such as Nafion (TM, produced by DuPont, and the same applies to the following) is generally used. The polymer compound has a hydrophobic main chain 100 and a side chain 101 having a hydrophilic ion-exchange group, as shown in FIG. 1. The hydrophilic ion-exchange group consists of a sulfone group ($SO_3^-$), for example.

Such an electrolyte is dissolved in a solvent. The solvent comprises a mixture of water and an organic solvent. An electrolyte solution is mixed with a catalyst to become a catalyst paste.

In the electrolyte solution, there is the following relationship between the electrolyte and a water content.

When the concentration of water in the electrolyte solution is reduced, even if the concentration of the electrolyte in the electrolyte solution is the same, the viscosity of the electrolyte solution is increased, and, on the other hand, when the concentration of water is increased, the viscosity of the electrolyte solution is reduced. This reason is estimated as follows.

Namely, when the concentration of water in the electrolyte solution is high, it is in such a state that water is adsorbed to the side chain 101 of an electrolyte 82 and a solid content of the electrolyte 82 aggregates in the electrolyte solution, as shown in FIG. 1A, and the viscosity of the electrolyte solution is reduced. When the concentration of water in the electrolyte solution is slightly reduced, the solid content of the electrolyte 82 is opened in the electrolyte solution by an action of an organic solvent contained in the electrolyte solution, as shown in FIG. 1B, and the viscosity of the electrolyte solution is increased because the solid contents are entangled with one another.

When the reaction layer is formed by mixing the electrolyte solution containing the solid content of the electrolyte 82 (FIG. 1A) in which the aggregation progresses, it is considered that the reaction layer is in a state shown in FIG. 2. Namely, since the solid content of the electrolyte 82 aggregates, the side chain 101 extends in multi-directions. Then, the side chain 101 and water in the reaction layer are adsorbed with each other, whereby a hydrophilic region 83 is dispersed in the reaction layer to be formed. Thus, at a position where the solid content of the electrolyte 82 aggregates in the reaction layer, it is difficult for a proton and water to move in the reaction layer due to ion resistance in the reaction layer. Thus, in a low humidification state, an electrolyte film and the electrolyte 82 in each catalyst layer are dried to cause reduction of performance, and in an excessively humidified state, this causes reduction of performance due to flooding.

In other words, in order to make the hydrophilic group of the electrolyte (side chain 101) to face the catalyst to reliably form the hydrophilic region between the electrolyte and the catalyst, it is preferable that the electrolyte in the electrolyte solution is in a state of FIG. 1B. To do this, the water content of the electrolyte solution is set to not more than 10% by weight of the electrolyte solution, as described above.

It is considered that when the electrolyte in a state of FIG. 1B is used, a cathode catalyst layer is in a state of FIG. 3B.

The side chain 101 of the electrolyte 82 is in a state of extending in one direction, and thus, in a catalyst paste, that is, in a reaction layer for a fuel cell, the hydrophilic ion-exchange group (sulfone group) adsorbs water in a pre-paste. Thus, as shown in FIG. 3, in the reaction layer, a hydrophilic group 101 of the electrolyte 82 is in a state of facing a surface of the catalyst 81, and the hydrophilic region 83 is formed between the electrolyte 82 and the catalyst 81. It is considered that the sulfone group is adsorbed to water in the pre-paste as described above, whereby the hydrophilic regions 83 are continuously formed around the catalyst 81, and the hydrophilic regions 83 are formed while communicating with each other. Thus, in the reaction layer using the catalyst paste, a proton and water easily move as shown in FIG. 3 and an electrochemical reaction smoothly progresses. Even when the fuel cell having such a reaction layer is in any of the low humidification state and the excessively humidified state, the power generation capacity can be increased.

See Japanese Application No. 2010-002362 for details.

As a functional group having an affinity for the hydrophilic group of the electrolyte, at least one kind selected from a nitric acid group, an amino group, a sulfonic acid group, a hydroxyl group, and a halogen group can be used. When the hydrophilic group of the electrolyte is the sulfonic acid group, the functional group is preferably a nitric acid group, an amino group, or a sulfonic acid group, more preferably a nitric acid group.

Although a method of making the functional group to have an affinity for the hydrophilic group of the electrolyte is not limited particularly, it is preferable that the functional group is previously imparted to the catalyst side. The affinity means a state in which the functional group is chemically adsorbed to the hydrophilic group.

When the functional group is introduced to the catalyst, it is preferable that the functional group is concentrated on a catalyst metal particle of the catalyst. This is because when the electrolyte solution and the catalyst are mixed, if the functional group is dispersed, the functional group interferes with the hydrophilic group of the electrolyte, and the electrolyte may be unable to be maintained in an opening state (see, FIG. 1B).

In order to concentrate the functional group on the catalyst metal particle, a metal complex which is the same as or similar to the catalyst metal particle and contains the functional group is bound to the catalyst metal particle.

When a platinum particle or a platinum-alloy particle is employed as the catalyst metal particle, the catalyst metal (Pt) particle can be modified by using the following solutions.

(1) Functional Group: Examples of Nitric Acid Group

Diammine dinitro platinum (II) nitric acid fluid (cis-[Pt$(NH_3)_2(NO_2)_2$]/$HNO_3$ sln.)

The same product subjected to aging treatment (cis-[Pt$(NO_2)_4$]/$HNO_3$ sln.)

Hexahydroxo platinum (IV) acid nitric acid solution (($H_2Pt(OH)_6$)/$HNO_3$ sol.)

(2) Functional Group: an Example of Sulfonic Acid Group

Hexahydroxo platinum (IV) acid sulfuric acid solution (($H_2Pt(OH)_6$)/$H_2SO_4$ sol.)

(3) Functional Group: an Example of Amino Group

Tetraammine platinum (II) hydroxide aqueous solution ([Pt$(NH_3)_4(OH)_2$]/$H_2O$ sln.)

When a fuel cell reaction progresses in the reaction layer, accompanying generation and movement of generated water, the functional group concentrated on the catalyst metal particle is separated from the catalyst metal particle and dispersed in the reaction layer, whereby the functional group is bound to the hydrophilic group of the electrolyte in the reaction layer.

The functional group may not be previously introduced to the catalyst side, but the functional group may be introduced to the catalyst paste or the reaction layer afterward.

In order to apply the functional group across the entire reaction layer, preferably, after the functional group is introduced to the reaction layer, the fuel cell reaction is executed to generate the generated water, and the generated water is moved. At this time, preferably, the fuel cell reaction is under a high humidification condition and is generated water-rich.

In the amount of the functional group to be introduced to the reaction layer, although an equivalent thereof should be not less than the equivalent of the hydrophilic group, it is preferable from the standpoint of executing the fuel cell reaction that the introduction amount of the functional group is 0.05 to 0.6 equivalent.

Of course, when a large amount of the functional group is infiltrated in the reaction layer, a sensitive layer can be made to have a uniform affinity for the hydrophilic group of the electrolyte of the entire reaction layer.

After the functional group is made to have an affinity for the hydrophilic group of the electrolyte, a metal ion capable of forming a complex with the functional group is introduced to the reaction layer.

Although a method of introducing the metal ions is not limited particularly, a method of infiltrating the reaction layer in an aqueous solution of the metal ions can be employed.

When a nitric acid group is employed as the functional group, ruthenium ions and osmium ions may be used, and they each form a nitrosyl complex.

In other functional groups, suitable metal ions are employed.

In the introduction amount of the metal ions, the equivalent is not less than the equivalent of the hydrophilic group of the electrolyte contained in the reaction layer.

In order to remove the functional group made to have an affinity for the hydrophilic group of the electrolyte and unreacted metal ions, the reaction layer is cleaned. If the fuel cell reaction can be performed after the introduction of the metal ions, extra metal ions can be removed by the generated water.

MODE FOR CARRYING OUT THE INVENTION

A carbon supported catalyst was prepared as a raw material catalyst. In the raw material catalyst, a carbon black particle is a carrier, and the carbon black particle is made to carry a catalyst platinum particle by a well-known method (supported amount: 50%).

1 g of the raw material catalyst was added to a nitric acid aqueous solution of diammine dinitro platinum (Pt 0.05/150 ml) whose nitric acid concentration is 0.07% (0.01 M) provided by FURUYA METAL Co., Ltd., and the solution was stirred by a stirrer for five hours at an indoor temperature. After that, filtration was performed, and drying was performed at 60° C. for two hours in an air atmosphere. In addition, heat treatment was performed at 150° C. for two hours under a nitrogen atmosphere. A final weight of a sample thus obtained was 1.012 g, and a Pt yield obtained from a Pt residual amount of a filtrate was 84.3%.

According to the above constitution, platinum of a complex is adsorbed to the catalyst platinum particle of the raw material catalyst, and the nitric acid group is present around the catalyst platinum particle.

Next, the obtained catalyst was ground. The ground catalyst was charged in a vessel with 100 ml of water and subjected to defoaming treatment using a hybrid mixer (HM-500 manufactured by KEYENCE CORPORATION). The amount of time of the defoaming treatment was four minutes.

After the defoaming treatment, the above solution was left on overnight, a supernatant solution was discarded, 10 g of electrolyte (5% aqueous solution of Nafion) was added, and stirring was performed (centrifugal stirring was performed (for four minutes) by the hybrid mixer).

A paste thus obtained was coated onto each diffusion layer on the hydrogen electrode side and the oxygen electrode side to be dried and, thus, to be formed as the reaction layer. The reaction layer was applied onto a solid polymer electrolyte membrane by hot pressing.

Figure 1:
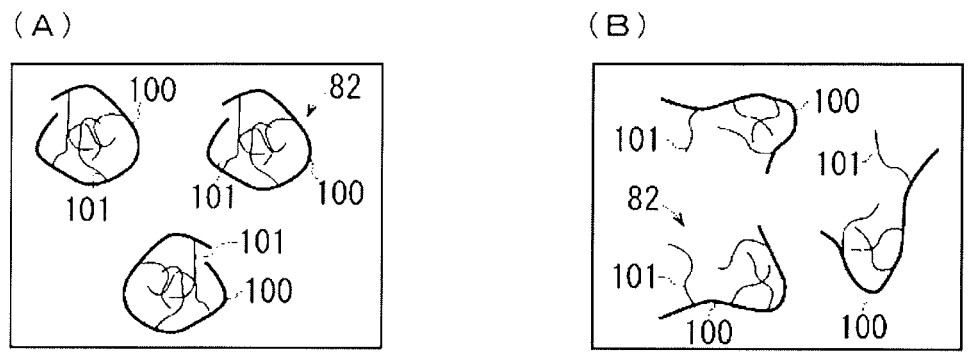
FIG. 1 is a schematic diagram showing a form of an electrolyte in an electrolyte solution.
Figure 2:
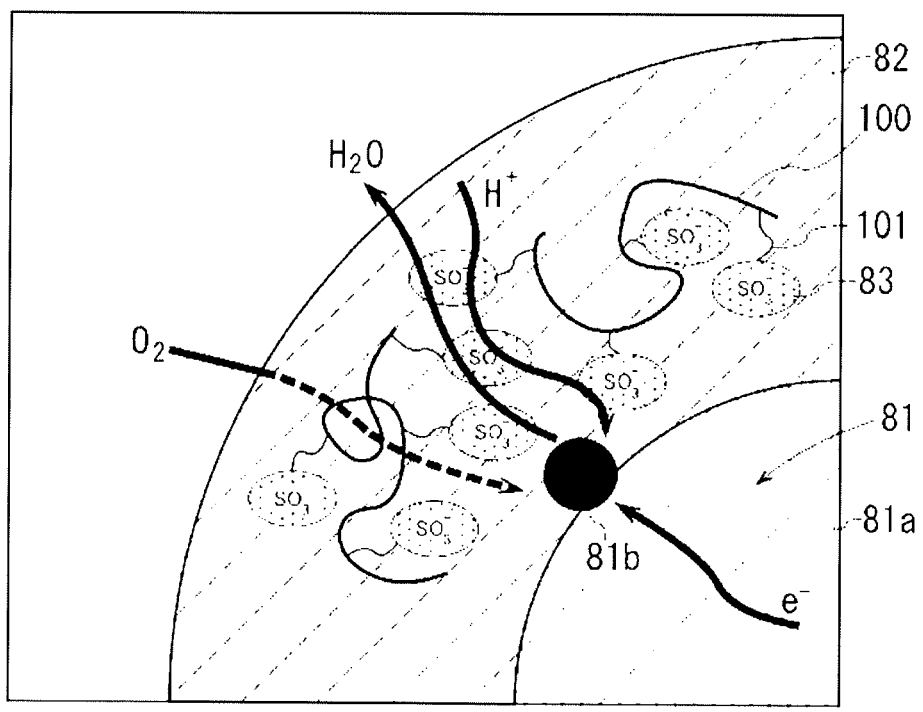
FIG. 2 is a schematic diagram for explaining a PFF structure corresponding to FIG. 1A.
Figure 3:
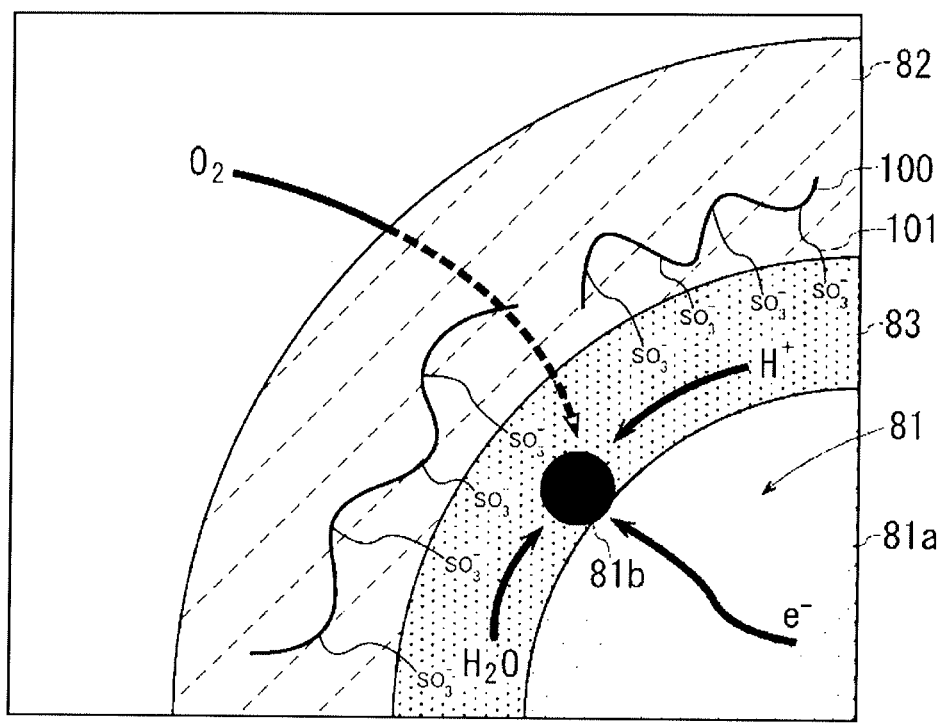
FIG. 3 is a schematic diagram for explaining the PFF structure corresponding to FIG. 1B.
Figure 4:
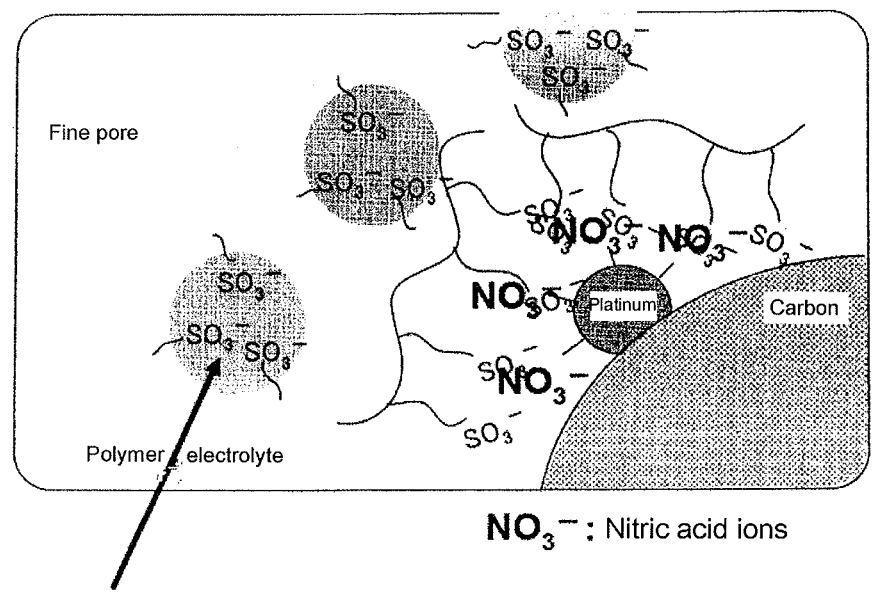
FIG. 4 is a schematic diagram showing a constitution of a reaction layer immediately after manufacturing in an embodiment.

In the reaction layer thus obtained, as shown in FIG. 4, a PFF structure is employed, and the nitric acid groups are present around the catalyst platinum particle.

Figure 5:
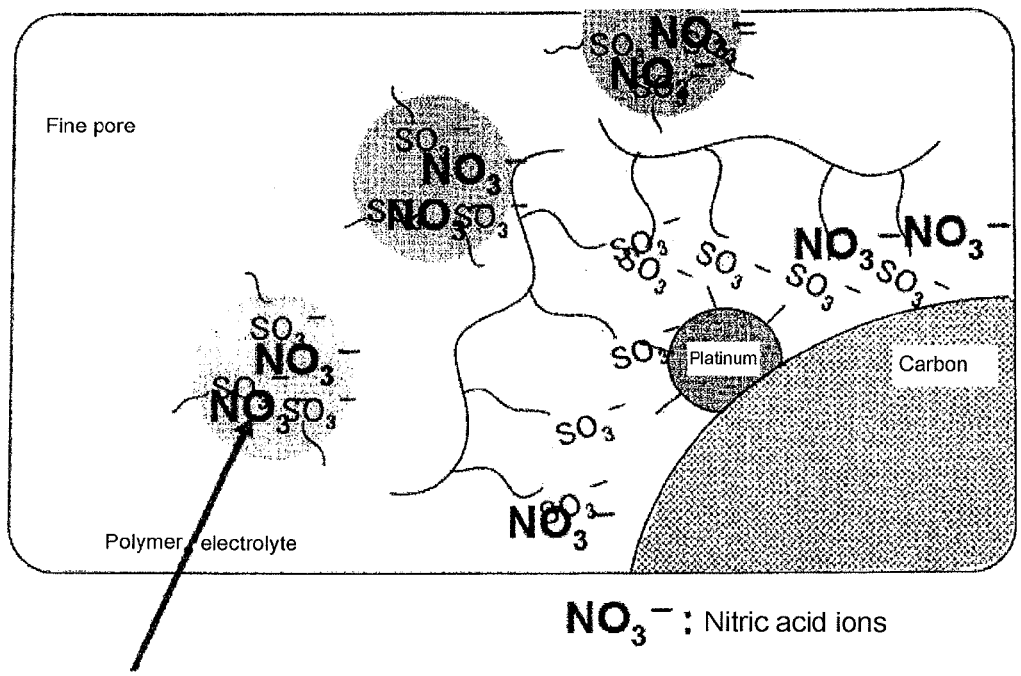
FIG. 5 is a schematic diagram showing a constitution of the reaction layer after execution of a fuel cell reaction.

In FIG. 5, although the hydrophilic region formed between the electrolyte layer and the catalyst is a main body of the PFF structure, it is considered that a sulfone group which cannot be oriented either in the electrolyte layer or on the catalyst side is hardened to form a cluster.

The fuel cell reaction was executed using a membrane electrode assembly thus obtained. When the fuel cell reaction is executed, a surface of the catalyst platinum particle is activated to facilitate separation of the nitric acid group, and, in addition, the nitric acid group is diffused over the entire reaction layer accompanying the generation and movement of the generated water.

The execution time of the fuel cell reaction is preferably 1 to 4 hours (high humidification condition).

Figure 6:
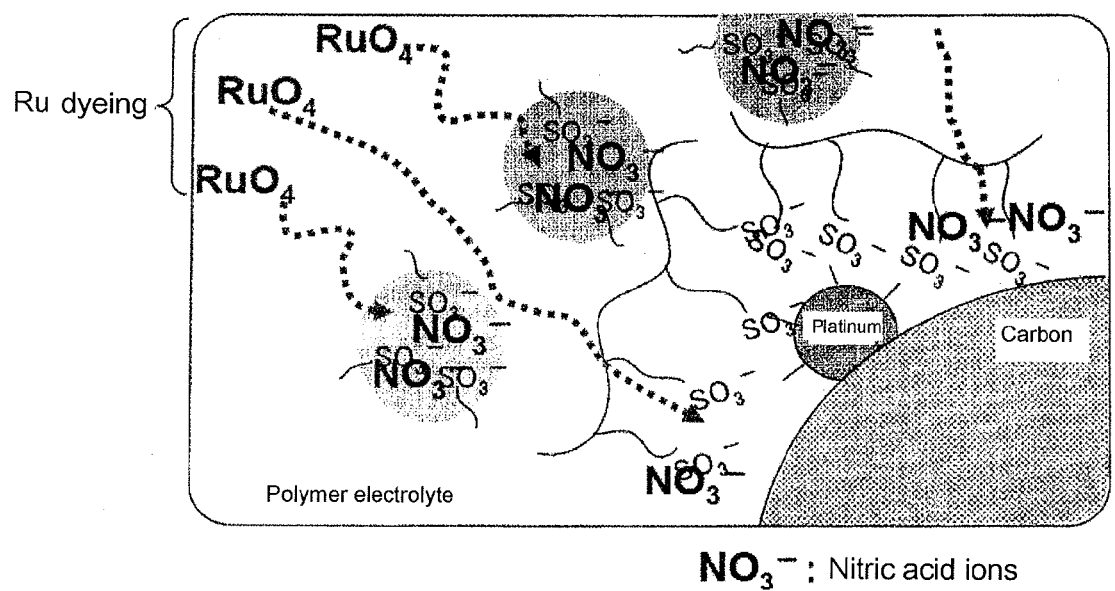
FIG. 6 is a schematic diagram showing dyeing using ruthenium ions.

Next, the reaction layer is cut out from the membrane electrode assembly and infiltrated in a ruthenium oxide solution, and, as shown in FIG. 6, the nitric acid group (nitric acid ions) is dyed with ruthenium.

At this time, when a sulfone group as a hydrophilic group aggregates (for example, the PFF structure and the cluster), the nitric acid group also aggregates. Accordingly, the nitric acid group dyed with ruthenium ions can be observed with a microscope (electron microscope).

Figure 7:
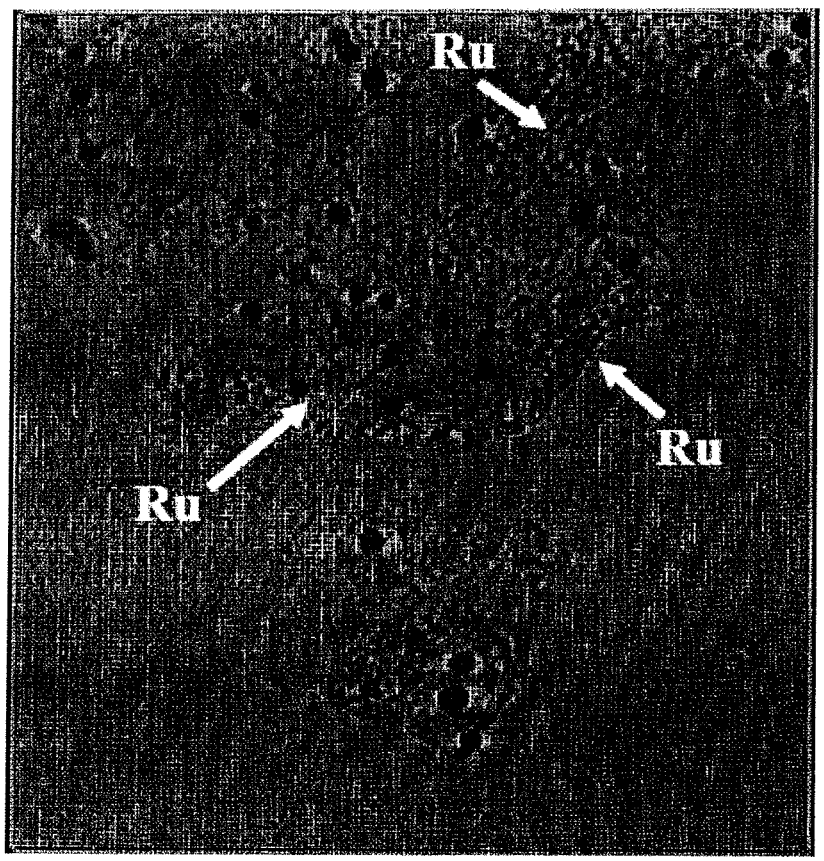
FIG. 7 is a 3D-TEM photograph of the ruthenium-dyed reaction layer.

A 3D-TEM observation image is shown in FIG. 7. A photograph shown in FIG. 7 is a cross-sectional imaging. In FIG. 7, large black circles show platinum particles, and small black points show ruthenium. A plain portion shows an electrolyte in which there is no catalyst or no hydrophilic group or the hydrophilic group is highly dispersed, and none of them substantially contribute to the movement of the proton.

The present invention is not limited to the description of the above embodiments and examples of the present invention. Various modified aspects are included in the present invention in the range in which those skilled in the art can easily conceive without departing from the description of the scope of claims.

EXPLANATION OF SYMBOLS

81 Catalyst
81*a* Carrier
81*b* Platinum catalyst particle
82 Electrolyte
83 Hydrophilic region

The invention claimed is:

1. A method of observing a fuel cell reaction layer comprising:
    making a functional group to have an affinity for a hydrophilic group of an electrolyte constituting a reaction layer of a fuel cell; and
    introducing a metal ion capable of forming a complex with the functional group to the reaction layer and dyeing the functional group with the metal ions,
    wherein the functional group is a nitric acid group, and the metal ion is a metal ion capable of forming a nitrosyl complex.

2. A method of observing a fuel cell reaction layer comprising:
- making a functional group to have an affinity for a hydrophilic group of an electrolyte constituting a reaction layer of a fuel cell; and
- introducing a metal ion capable of forming a complex with the functional group to the reaction layer and dyeing the functional group with the metal ions,
- wherein the metal ion is a ruthenium ion and/or an osmium ion.

3. A method of observing a reaction layer of a fuel cell, the reaction layer comprising a mixture of a catalyst having a platinum-based catalyst metal particle and an electrolyte, the method comprising the steps of:
- stirring the catalyst in an aqueous solution of a platinum complex having a nitric acid group, modifying a catalyst metal particle of the catalyst with the nitric acid group, and, at the same time, making the catalyst to have an affinity for water;
- mixing the catalyst made to have an affinity for water and a solution of the electrolyte to form a catalyst paste;
- forming the reaction layer of the fuel cell using the catalyst paste;
- making the nitric acid group to have an affinity for a hydrophilic group of the electrolyte of the reaction layer; and
- dyeing the nitric acid group with ruthenium ions.

* * * * *